Figure 1:
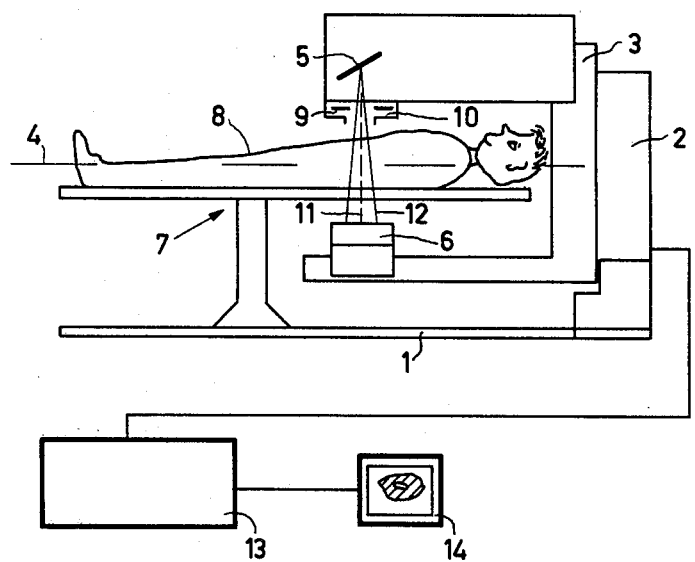

United States Patent [19]

Zieler

[11] 4,361,764

[45] Nov. 30, 1982

[54] DEVICE FOR DETERMINING LOCAL ABSORPTION DIFFERENCES IN AN OBJECT

[75] Inventor: Erich Zieler, Hamburg, Fed. Rep. of Germany

[73] Assignee: U.S. Philips Corporation, New York, N.Y.

[21] Appl. No.: 292,317

[22] Filed: Aug. 12, 1981

Related U.S. Application Data

[63] Continuation of Ser. No. 129,068, Mar. 10, 1980, abandoned.

[30] Foreign Application Priority Data

Mar. 27, 1979 [DE] Fed. Rep. of Germany ....... 2912010

[51] Int. Cl.³ .............................................. A61B 6/00
[52] U.S. Cl. .................................................... 378/14
[58] Field of Search ............................ 250/445 T, 505

[56] References Cited

U.S. PATENT DOCUMENTS

| 4,048,505 | 9/1977 | Hounsfield | 250/505 |
| 4,143,273 | 3/1979 | Richey et al. | 250/445 T |
| 4,200,799 | 4/1980 | Saito | 250/445 T |

Primary Examiner—Alfred E. Smith
Assistant Examiner—T. N. Grigsby
Attorney, Agent, or Firm—Jack E. Haken

[57] ABSTRACT

During computer tomography examinations, ring-like artefacts occasionally occur because the X-ray source becomes hot, so that the X-ray focus changes its position in space. Because the distance between the detector and the diaphragm which stops the radiation beam is several times larger than the distance between the X-ray focus and the diaphragm, the shifting of the radiation beam on the detector is even greater. If the detector consists of detection elements which are not exactly identical, it may occur that the sensetivities of the detection elements apparently change with respect to each other due to such a shift, the reconstruction then giving rise to said artefacts. In accordance with the invention, the position where the radiation beam is incident on the detector is measured and the diaphragm for the stopping of the radiation beam is readjusted so that the radiation is each time incident in the same area.

2 Claims, 4 Drawing Figures

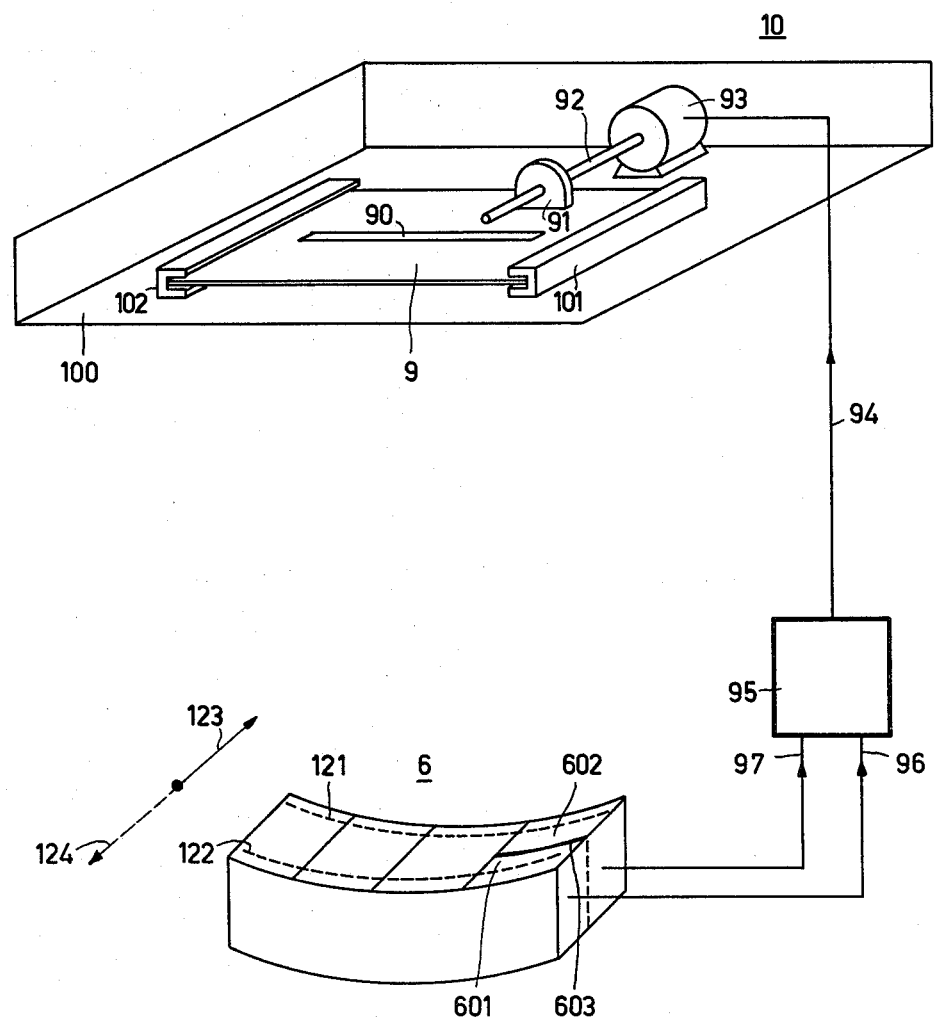
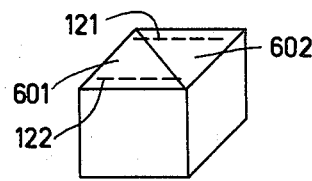
FIG.3
FIG.4

DEVICE FOR DETERMINING LOCAL ABSORPTION DIFFERENCES IN AN OBJECT

This is a continuation of application Ser. No. 129,068, filed Mar. 10, 1980, and now abandoned.

The invention relates to a device for determining local absorption differences in an object, comprising an X-ray source for generating a flat, fan-shaped X-ray beam for irradiating the object during an examination and an X-ray detector which comprises a large number of detection elements for measuring radiation transmitted by the object, the X-ray source comprising an X-ray tube which is arranged behind a diaphragm having a slit-shaped aperture.

A device of this kind is particularly suitable for medical X-ray diagnostics. During an examination, a part of the body of a patient is irradiated from different directions by means of the flat, fan-shaped X-ray beam and locally transmitted radiation is measured. From the measuring data thus obtained, the density distribution of the part of the body of the patient is calculated by means of a computer after which it is, for example, displayed on a television monitor.

German Offenlegungsschrift No. 27 23 073 describes a device of the described kind in which the X-ray source and the X-ray detector are mounted on a rotating holder which comprises a central aperture for accommodating an object to be examined. The X-ray source is arranged on one side of the central aperture and the X-ray detector is situated on the other side thereof. During an examination, the holder is rotated around the central aperture, so that a slice of the object arranged in this aperture is irradiated from different directions. The thickness of the slice examined is adjustable in that the width of the slit-shaped aperture of the diaphragm arranged in front of the X-ray tube can be adjusted.

If a layer of the object is irradiated a number of times in apparatus of the described kind, notably if these apparatus comprise detection elements of the ionization chamber type, irregularities occur in the images reconstructed from these exposures. These irregularities become manifest as more or less pronounced ring-like artefacts. These artefacts correspond to the artefacts which are liable to occur when the individual elements of the detector have a different sensitivity and the output signals of these elements are not corrected accordingly (recalibration) during the calculation by the computer. The ring-like artefacts, however, can also be observed in apparatus which have been exactly recalibrated.

The invention has for its object to provide a device of the kind set forth in which the said drawback is mitigated. To this end, a device of this kind in accordance with the invention is characterized in that the diaphragm and the X-ray tube can be moved with respect to each other by means of an adjusting member which is controlled by an auxiliary detector and by means of which they are always so adjusted with respect to each other during operation that the fan-shaped beam is always incident on the X-ray detector in a fixed, predetermined area.

The invention is based on the recognition of the fact that the location inside an X-ray tube where radiation is generated is liable to shift during operation. The shifting may be due, for example, to thermal expansion of components inside the X-ray tube. If the diaphragm is rigidly connected to the X-ray tube, the X-ray source will emit the X-ray beam in a slightly different direction and the beam will be incident on the X-ray detector in a slightly different area. The detector output signals may be influenced thereby, so that it seems as if the detector sensitivities change. These apparent sensetivity variations cause said artefacts.

It is to be noted that the invention can also be used in apparatus in which a large number of radiation sources are arranged to be stationary on an arc of a circle around the examination zone, the radiation which is emitted by successively actuated radiation sources and which passes through the examination zone being measured by means of a detector device which is also distributed over at least one half circle. The invention can furthermore be used in apparatus in which the anode of a separate X-ray tube encloses the examination zone at least semi-circularly, the X-ray focus being electronically shifted on the anode.

An embodiment in accordance with the invention will be described in detail hereinafter, by way of example, with reference to the accompanying diagrammatic drawing.

Figure 2:
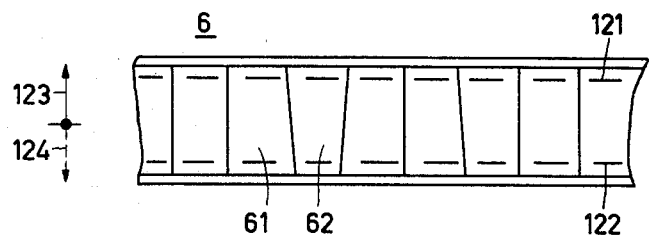

FIG. 1 shows a device for determining local absorption differences in an object in accordance with the invention, FIG. 2 shows a part of the X-ray detector, viewed from the X-ray source, FIG. 3 shows some details of the device shown in FIG. 1, and FIG. 4 shows a special embodiment of an auxiliary detector.

The apparatus shown in FIG. 1 comprises a supporting construction 2 which is rigidly connected to a base plate 1 and on which a frame 3 is journalled to be rotatable around a horizontal axis 4. One end of the rotary frame 3 accommodates an X-ray tube 5 (only diagrammatically shown), whilst on the other end a detector 6 is mounted, said detector and the X-ray tube 5 being situated in a common plane which extends perpendicularly to the axis of rotation 4. The detector 6 is shaped as an arc of a circle which extends through the plane of the drawing. It consists of a large number of separate detection elements which detect the radiation, for example, in accordance with the ionization chamber principle, each element comprising at least one high voltage electrode and one signal electrode which are directed onto the X-ray tube 5 and between which a pressurized gas, preferably xenon, is present, a voltage of approximately 2000 V being applied to said electrodes.

Between the X-ray tube 5 and the detector 6 there is arranged a patient examination table 7 on which a patient 8 is arranged so that the axis of rotation 4 extends through the patient and approximately parallel with respect to the longitudinal axis of the patient. On the X-ray tube 5 there is mounted a diaphragm housing 10 which inter alia accommodates a diaphragm 9 with a slit-shaped aperture, the edges of which extend perpendicularly to the plane of the drawing and which stops a radiation beam which passes through the patient and is incident on the detector 6. The central plane of the radiation beam 12, being denoted by broken lines and the reference numeral 11, extends perpendicularly to the axis of rotation 4. The "thickness" of the X-ray beam stopped by the diaphragm 9 usually amounts to from 3 to 30 mm at the area of the axis of rotation 4.

The system formed by the X-ray tube 5 and the detector 6 can be rotated around the axis of rotation 4 by means of a motor (not shown) which is arranged in the supporting construction and which rotates the frame 3. The patient is then irradiated from a number of directions, each detection element of the detector 6 supplying a measuring value after each rotation through a given angle (for example 1°). From the measuring values thus obtained, the absorption distribution in the plane of examination 11 is calculated by means of a computer 13, said distribution being displayed on a television monitor 14.

During operation it may occur that the focus of the X-ray tube 5, emitting the radiation beam 12 and assumed to be point-shaped in FIG. 1, shifts slightly in the direction parallel to the axis of rotation 4, i.e to the plane of examination. A feasible cause is, for example, the heating of the X-ray tube. For the X-ray tube use is customarily made of rotary-anode X-ray tubes, the drive shaft of the anode disc extending parallel to the axis of rotation 4. When the anode disc becomes hot, the drive shaft also becomes hot and expands, so that the X-ray focus of the X-ray tube 5 is shifted slightly to the left or the right, parallel to the axis 4. Because the distance between the focus of the X-ray tube 5 and the diaphragm 9 is small in comparison with the distance between the X-ray tube 5 and the detector 6 (for example, only one tenth of the latter distance), the area on the detector where the radiation beam 12 is incident is shifted substantially further.

FIG. 2 shows a part of a detector, viewed from the location of the X-ray tube 5. The boundary lines of the area of the detector 6 which is irradiated by the radiation beam 12 are denoted by broken lines and the reference numerals 121 and 122 in FIG. 2. When the X-ray focus shifts to the left or to the right in FIG. 1, the area on which the radiation beam is incident in FIG. 2 is shifted in the direction of the arrow 123 or the arrow 124, respectively, that is to say upwards and downwards, respectively, so that the boundary lines 121 and 122 are also shifted in the same direction.

The invention is based on the recognition of the fact that the ring-shaped artefacts mentioned in the preamble can be caused by such a shift. As is shown in FIG. 2 (in exaggerated form), the individual detection elements of the detector 6 are not identical. In a detector operating according to the ionization chamber principle, for example, the partitions of the ionization chambers constituting the individual detection elements are liable to be slanted with respect to each other, so that, for example, the detection element 61 in FIG. 2 is narrower at its top than at its bottom whilst the top of the detection element 62 is wider than its bottom.

A first consequence of these irregularities consists in that the signals of the detection elements, for example, 61 and 62, may deviate from each other when they are exposed to radiation of the same intensity. However, this effect is not disturbing, because a relevant correction can be made in that the measuring values supplied by the detection elements 61 and 62 are weighted with calibration factors prior to the reconstruction of the absorption distribution, said calibration factors being inversely proportional to the different sensitivities of the detection elements, so that the values used for the reconstruction are equal when the associated detection elements are exposed to radiation of the same intensity.

However, the shifting of the radiation beam 12 on the detector 6 also changes (at the same radiation intensity) the measuring values supplied by the individual detection elements. For example, if the area which is defined by the boundary lines 121 and 122 and on which the radiation is incident is displaced in the upward direction, the output signal of the detection element 61, possibly weighted with a constant calibration factor, becomes smaller, whilst the corresponding signal from the chamber 62 becomes larger, because the irradiated area (or the irradiated volume in the case of ionization chambers) of the detection element 61 decreases and the irradiated area of the detection element 62 increases. Thus, shifting of the radiation beam on the detector has exactly the same effect as if the sensitivities of the individual detection elements were changed, to a different extent.

Moreover, shifting of the radiation beam during an exposure also changes the irradiated volume, which may also cause errors during the reconstruction.

Even though both described effects are comparatively weak (for example, the sensitivities of the chambers are changed by hardly more than 1%), they cause major artefacts which disturb the diagnosis during the reconstruction, because the known reconstruction methods react very critically to such measuring errors.

Artefacts of this kind are eliminated to a high degree by the device shown in FIG. 3. FIG. 3 shows the diaphragm housing 10, the front wall and one side wall having been omitted. On a base plate 100 of the diaphragm housing 10 there are arranged two guide rails 101 and 102 so that they extend parallel to the axis of rotation 4 and perpendicularly to the plane of examination. In these guide rails the diaphragm 9, having an aperture 19 which extends horizontally and perpendicularly to the guide rails 101 and 102, is arranged to be displaceable. On the diaphragm 9 which is displaceable parallel to the axis of rotation 4 (FIG. 1) and perpendicularly to the plane of examination there is secured a threaded nut 91 which cooperates with a shaft 92 which is driven by a motor 93 mounted on the base plate 100. During operation of the motor 90, the nut 91 and hence the diaphragm 9 is displaced in the one or in the other direction, depending on the direction of rotation, parallel to the axis of rotation 4 and perpendicularly to the plane of examination, so that the X-ray beam stopped by the diaphragm 9 can be displaced in the direction of the arrows 123, 124 (FIG. 2).

The shifting of the X-ray beam on the detector 6, caused by the shifting of the focus, can in principle also be compensated for by shifting the diaphragm 9, by means of the motor 93, in the same direction and to substantially the same extent as the focus, so that the position of the radiation beam on the detector 6 is maintained. To this end, the motor is controlled by a controller 95 via a control line 94. The controller comprises two inputs 96 and 97 and is constructed so that the motor rotates in one direction for as long as the signal on the line 96 exceeds the signal on the line 97, and that the direction of rotation is reversed when the signal on the line 97 becomes larger than that on the line 96. If desired, the number of revolutions can also be controlled so that the motor operates at a high speed in the case of a large deviation of the signal values on the inputs 97 and 96 and at a low speed when the deviation is small. The motor stops when the difference between the two input signals (almost) reaches the value zero.

The inputs 96 and 97 of the controller are connected to the outputs of two measuring cells 601 and 602 which are arranged one adjacent the other so that a connecting line between the two centres thereof extends parallel to the axis of rotation, i.e. the measuring cells 601 and 602 are symmetrically arranged with respect to the central plane or the plane of examination 11 (FIG. 1). The measuring cells 601 and 602 are situated in the beam path (behind the patient 8 and the table 7) and preferably form part of the detector 6. When the detection elements of the detector 6 operate according to the ionization principle, the measuring cells 601 and 602 are ionization chambers. These chambers can be simply realized by dividing the signal electrode of an ionization chamber into two halves which are electrically insulated from each other and which are connected to the inputs 96 and 97, a partition 603 being suitably provided in the symmetry plane between the two halves.

When a desired area of the detector which is defined by the boundary lines 121 and 122 is exposed to the radiation not absorbed by the body 8 and the table 7, the output signals of the measuring cells 601 and 602 are equal, assuming that the absorption in the zone of the body between the measuring cells 601 and 602 and the X-ray source 5, 9 (FIG. 1) does not abruptly change in the direction perpendicular to the plane of examination.

If the X-ray focus shifts parallel to the axis of rotation (perpendicularly to the plane of examination), the radiation beam (121, 122) on the detector 6 shifts in the opposite direction and over a larger distance, the ratio of the signals on the inputs 96 and 97 then changing so that the motor is switched on. The motor displaces the diaphragm 9 so that the predetermined ratio of the signals of the measuring cell 96, 97, and hence the predetermined position of the radiation beam with respect to the detector is restored again.

Thus, there is obtained a control circuit which ensures that the radiation beam in the direction perpendicular to the plane of examination is always incident on the same area of the detector 6.

Even though the invention has been described on the basis of detector elements operating according to the ionization chamber principle, the same artefacts can occur when use is made of other detection elements which likewise are not exactly identical as far as their geometry and sensitivity are concerned. Notably when use is made of crystal detectors, the measuring cells 601 and 602 may also be shaped as triangles (see FIG. 4) which together form a cube. It is important only that the ratio of the output signals of the two measuring cells 601 and 602 changes when the irradiated surface on the detector, bounded by the lines 121 and 122, shifts perpendicularly to the plane of examination (parallel to the axis of rotation 4), so that therefrom a control signal can be derived for the displacement of the diaphragm 9.

The measuring cells 601 and 602 can also be arranged inside the detector device, i.e. between two detection elements. By addition of the output signals of the measuring cells 601 and 602, a signal is then obtained which represents the absorption of the body at the area corresponding to the measuring cell, and which can also be used for the reconstruction of the absorption distribution. Preferably, pairs of measuring cells 601 and 602 are arranged at different locations of the detector, the output signals of the detection elements present at the same side of the plane of examination each time being added and the sum signals thus obtained being applied to the inputs 96 and 97. Any effect of an inhomogeneous absorption distribution in the direction perpendicular to the plane of examination on an individual pair of measuring cells can thus be reduced.

Thus far, the cause of the shifting of the X-ray focus in the X-ray tube was stated to be the heating of the anode disc during operation. A shift of this kind, however, can also be caused by mechanical vibrations during the rotation or by elastic deformations. The described ring-shaped artefacts are again avoided to a high degree in the device in accordance with the invention.

In the embodiment shown in FIG. 3, the diaphragm is formed by a simple diaphragm plate 9, the "thickness" of the radiation beam (distance between the lines 121 and 122) being determined by the width of the slit 90. Alternatively, use can be made of a diaphragm which consists of two parts which are displaceable with respect to each other, the distance between said parts determining the thickness of the radiation beam. The diaphragm must then be displaced as a unit perpendicularly to the plane of examination, i.e. to the diaphragm edges.

What is claimed is:

1. A device for determining local absorption differences in an object, comprising an X-ray source for generating a flat, fan-shaped X-ray beam for irradiating the object during an examination, and an X-ray detector which comprises a large number of detection elements for measuring radiation transmitted by the object, the X-ray source comprising a diaphragm having a slit-shaped aperture and an X-ray tube which is arranged behind the diaphragm, characterized in that the device further comprises adjusting means for moving the diaphragm and the X-ray tube with respect to each other and an auxiliary detector for controlling the adjusting means so that the fan-shaped beam is always incident on the X-ray detector in a fixed, predetermined area.

2. A device as claimed in claim 1, further comprising a controller comprising two inputs and a pair of auxiliary detectors which are adjacently arranged in the direction transverse to the flat X-ray beam, the output signals of said auxiliary detectors being equal if the radiation beam is incident on the detector in the predetermined area and being unequal if this is not the case, the auxiliary detectors being connected to the inputs of the controller and the controller being connected to operate the adjusting means.

* * * * *